United States Patent
Radice et al.

(10) Patent No.: US 6,699,471 B2
(45) Date of Patent: Mar. 2, 2004

(54) INJECTABLE HYALURONIC ACID DERIVATIVE WITH PHARMACEUTICALS/CELLS

(75) Inventors: Marco Radice, Modena (IT); Andrea Pastorello, Abano Terme (IT); Alessandra Pavesio, Padua (IT); Lanfranco Callegaro, Thiene (IT)

(73) Assignee: Fidia Advanced Biopolymers, SRL, Abano Terme (IT)

( * ) Notice: Subject to any disclaimer, the term of this patent is extended or adjusted under 35 U.S.C. 154(b) by 0 days.

(21) Appl. No.: 09/887,757

(22) Filed: Jun. 21, 2001

(65) Prior Publication Data

US 2002/0076810 A1 Jun. 20, 2002

Related U.S. Application Data

(63) Continuation of application No. PCT/IB99/02077, filed on Dec. 21, 1999.

(51) Int. Cl.[7] .................................................. C12N 5/00
(52) U.S. Cl. ........................................ 424/93.7; 514/54
(58) Field of Search ............................. 514/54; 424/93.7

(56) References Cited

U.S. PATENT DOCUMENTS

| | | | | |
|---|---|---|---|---|
| 4,801,619 A | | 1/1989 | Lindblad ..................... | 514/42 |
| 4,851,521 A | * | 7/1989 | della Valle et al. ........ | 536/55.1 |
| 5,516,532 A | | 5/1996 | Atala et al. ................. | 424/548 |
| 5,723,331 A | | 3/1998 | Tubo et al. ................. | 435/366 |
| 5,776,193 A | | 7/1998 | Kwan et al. ................ | 424/423 |
| 5,786,217 A | | 7/1998 | Tubo et al. ................. | 435/402 |
| 5,939,323 A | * | 8/1999 | Valentini et al. ............ | 435/395 |
| 5,968,556 A | | 10/1999 | Atala et al. ................. | 424/548 |
| 5,972,385 A | | 10/1999 | Liu et al. .................... | 424/486 |
| 5,972,703 A | | 10/1999 | Long et al. ................. | 435/372 |

FOREIGN PATENT DOCUMENTS

| | | | | |
|---|---|---|---|---|
| CH | 1204245 | | 1/1999 | |
| EP | 341745 | * | 11/1989 | ........... C08B/15/00 |
| EP | 92309544 | | 10/1992 | |
| EP | 96303383 | | 5/1996 | |
| EP | 98107889 | | 4/1998 | |
| EP | 88420194 | | 6/1998 | |
| WO | WO 9012603 | | 11/1990 | |
| WO | WO 9901143 | | 1/1991 | |
| WO | WO 9118558 | | 12/1991 | |
| WO | WO 9415653 | | 7/1994 | |
| WO | WO 9705863 | | 2/1997 | |
| WO | WO 9732591 | | 9/1997 | |

* cited by examiner

Primary Examiner—Jean C. Witz
(74) Attorney, Agent, or Firm—Birch, Stewart, Kolasch & Birch, LLP

(57) ABSTRACT

Disclosed is an injectable, biocompatible and biodegradable composition, comprising at least one hyaluronic acid benzyl ester or auto-cross-linked derivative, in combination with at least one mammalian cell and/or at least one pharmacologically or biologically active substance and/or micro-particles such as fibres, granules, microspheres or sponge fragments of a hyaluronic acid derivative.

12 Claims, No Drawings

INJECTABLE HYALURONIC ACID DERIVATIVE WITH PHARMACEUTICALS/CELLS

This application is a Continuation of PCT International Application No. PCT/IB99/02077 filed on Dec. 21, 1999, which was published in English and which designated the United States and on which priority is claimed under 35 U.S.C. §120, the entire contents of which are hereby incorporated by reference.

SUBJECT OF THE INVENTION

The present invention is directed to an injectable, biocompatible and biodegradable composition, comprising at least one hyaluronic acid benzyl ester or auto-cross-linked derivative, in combination with at least one mammalian cell and/or at least one pharmacologically or biologically active substance and/or micro-particles such as fibres, granules, microspheres or sponge fragments of a hyaluronic acid derivative.

BACKGROUND OF THE INVENTION

Although injectable compositions and carriers for such compositions have been known in the art, there still exists a need for injectable compositions which are biocompatible, are biodegradable, offer protective aspects to the active component, and provide enhanced bioavailability of the active components. This is important, for instance, in the field of joint cartilage repair.

The aim of joint cartilage repair is to restore the surface of the joint, reduce pain and prevent further deterioration of the tissues. Many methods have been applied to date for the treatment of cartilage defects, each of which has presented disadvantages (Tom Minas et al., "Current Concepts in the treatment of Articular Cartilage Defects", Orthopedics, June 1997, vol. 20, No. 6).

The marrow stimulation technique consists of reaching subchondral bone tissue areas by means of abrasion or perforation, thus stimulating the formation of a fibrin 30 clot containing pluripotent stem cells. The clot subsequently differentiates and takes shape, forming fibrocartilage repair tissue. However, this tissue does not have the mechanical properties or the physiological and structural characteristics of healthy, lasting joint cartilage.

Another technique consists of implanting into the site of the defect a piece of periosteal and perichondral tissue taken, for example, from the rib cartilage. Such treatment does trigger the development of hyaline cartilage, but the repair tissue is poorly integrated with the surrounding healthy tissues and the implanted tissue subsequently becomes ossified.

Autologous and homologous osteochondral grafts are invasive, require complex surgical techniques and carry the risk of, for example, viral infection.

Other attempts to reconstruct the joint cartilage consist of implanting synthetic matrices with allogenic chondrocytes dispersed within them, or growth factors able to stimulate the proliferation of the chondrocytes. These methods require that the cartilage tissue is grown in vitro and then implanted into the defect. The synthetic matrices most commonly used are collagen gels, matrices of polyanhydrides, polyorthoesters, polyglycolic acid and its copolymers. The chief disadvantage of the use of such matrices is represented by the immune response directed against the implanted material. Chondrocytes are known to be cultured in gel constituted by agarose, hyaluronic acid, fibrin glue, collagen and alginate. However, these cultures in gel do not provide the mechanical stability necessary for them to adhere to the site once implanted and to allow the reconstruction of the cartilage structure. Moreover, chondrocyte cultures in substances such as fibrin de-differentiate into cells which appear to be similar to fibroblasts. Lastly, although gels constituted by substances such as agarose induce chondrocyte re-differentiation, the use of this compound has not been approved for internal applications to humans.

Joint cartilage defects have also been treated with suspensions of isolated chondrocytes in the absence of supporting matrices. It is thought, however, that chondrocytes lose their viability and/or do not remain at the site of the defect and that they form fibrocartilage or islets of cartilage immersed in fibrous tissue (see U.S. Pat. No. 5,723,331).

Some biological materials consisting of hyaluronic acid derivatives have been used to fabricate porous degradable scaffolds for tissue repair, reconstruction and wound healing (WO 97/45532). Others have been shown to support the growth of poor resistant and weak cells (WO 98/56897). These materials, however, are not injectable.

These disadvantages of the prior art are overcome by the present invention by providing an injectable composition such as one containing chondrocytes or bone marrow stroma cells dispersed in a gel containing at least one hyaluronic acid benzyl ester derivative or auto-cross-linked derivative.

Various pieces of evidence have emerged in the literature (see enclosed abstract) recently concerning the use of cell suspensions for injection purposes, in particular keratinocytes for the treatment of chronic ulcers and burns. See Silverman et al, Plast. Reconstr. Surg., June 1999, 103(7) 1809–18 (combination of fibrinogen and chondrocytes); Atala et al., J. Urol., Aug. 1993, 150 (2 Ptd. 2) p. 745–7 (chondrocyte-alginate gel)). Keratinocyte cultures can be developed according to various methods cited in the literature (in the presence or absence of foetal calf serum, with chemically defined culture medium, etc.). These cultures are then vehicled in the host bed suspending them in various media, one of the most frequently cited of which is fibrin both of autologous and commercial origin. There are considerable disadvantages to the use of such methods. Firstly, the cell suspension has to be prepared immediately before use, so the cells have to be stored in a medium with a different composition from the one used for their application, while other problems may arise with the fibrin glue used as a vehicle, particularly when this is not autologous.

These problems are overcome by the present invention by dispersing epithelial cells (such as keratinocytes) or derivatives of other embryonic origin in a hyaluronic-acid-based medium for various reasons. The preparation is perfectly biocompatible and biologically safe and the cell survival rate is higher than in cell suspensions in completely liquid media. This last point in particular is important. In cases where the patient or application site is a long distance from the site of production for the component, safe transport becomes a problem. The product will inevitably be shaken about during transport damaging the cells, and this problem needs to be solved. However, when the cells are dispersed in a highly viscous medium according to the present invention, this problem is overcome because the host medium acts as a cushion. Another advantage derives from the possibility of spreading the cell suspension efficiently over the surface to be treated, which is a simpler way of applying it than the methods currently used, involving sprays based on fibrin glue.

Another application of the present invention concerns the possibility of suspending the cells in the medium and then applying them by injection. Other non-limiting applications are the administration of fibroblasts (autologous) for aesthetic surgical purposes or as fillers for tissue defects, preparations of adipocytes (autologous, heterologous or homologous) for soft tissue augmentation for applications such as the reconstruction of breasts or other soft body parts, injections of urethral cells such as fibroblastoids or cartilage cells for the treatment of urinary incontinence. In all these examples, the Hyaluronic acid-based material has the double function of acting as a vehicle for injections and of protecting the cell preparation during transport.

As is known, hyaluronic acid plays a vital role in many biological processes such as tissue hydration, proteoglycan organization, cell differentiation, proliferation and angiogenesis (J. Aigner et al. L. Biomed. Mater. Res. 1998, 42, 172–181). Hyaluronic acid derivatives maintain all the properties of said glycosaminoglycan, with the advantage of being able to be processed in various forms and having solubility and degradation times which vary according to the type and percentage of derivation (EP 0216453 B1). Moreover, the hyaluronic acid derivatives offer new properties due to the insertion of specific molecules in the structure of the hyaluronic acid. For example, the sulfated derivatives of hyaluronic acid have anticoagulant properties and are resistant to hyaluronidase (WO 95/25751). It has been demonstrated that said compositions do not trigger immune responses by the organism and the chondrocytes they contain maintain their phenotype. Hyaluronic acid derivatives are not cytotoxic and allow the synthesis of components of the extracellular matrix that are necessary for the development of the cartilage tissue. Moreover, said derivatives do not represent a simple vehicle for the cells but are able to stimulate their poliferation and, as they degrade, allow the development of the cells into three-dimensional structures. Besides stimulating the growth of implanted cells, the hyaluronic acid derivatives are able to create an extracellular environment similar to that of mammal foetuses which stimulates the regeneration of tissues. Moreover, as the hyaluronic acid derivatives degrade, they release oligomers, stimulating the recruitment of progenitor cells of chondrocytes and favouring their development towards the chondrocyte cell line. Such hyaluronic acid derivatives have been proposed for use in treatment of arthropathies (WO 97/49412).

It is known that hyaluronic acid derivatives can be used as three-dimensional, solid scaffolds in the form of non-woven fabrics, sponges, granules, microspheres, tubes and gauzes to grow stem cells in vitro (WO 97/18842), in the form of non-woven fabrics associated with a perforated membrane for the growth in vitro of fibroblasts and keratinocytes (WO 96/33750) and in the form of non-woven fabrics for the growth of chondrocytes (J. Aigneretal., L. Biomed. Mater. Res., 1998, 42, 172–181). However, to date, nobody has made an injectable gel containing hyaluronic acid derivatives and mammalian cells, such as chondrocyte cells, that allows the surgeon to use only mildly invasive surgical techniques, such as endoscopic surgery, enabling the cells to be incorporated in a composition to survive transport and completely fill irregularly-shaped lesion sites.

Unlike the method of seeding of cells on solid supports, in the present invention the cells are evenly dispersed in all three dimensions throughout the composition in the form of a gel made according to the present invention. Said compositions allow the regenerated tissue to integrate perfectly with the cartilage tissue surrounding the defect. The compositions according to the present invention can be used to advantage for the treatment of both superficial and deep cartilage defects. Superficial defects are those affecting the cartilage tissue alone, while deep defects are those which also involve the subchondral bone tissue and the layer of calcified cartilage between the subchondral bone tissue and the cartilage.

DETAILED DESCRIPTION OF THE INVENTION

The present invention concerns injectable, biocompatible and biodegradable compositions containing at least one hyaluronic acid benzyl ester derivative and/or auto-cross-linked derivative, at least one pharmacologically and/or biologically active substance, such as a growth factor, and/or at least one mammalian cell, particularly chondrogenic cells.

1. The Hyaluronic Acid Component

The present invention, therefore, describes injectable biocompatible compositions based on a benzyl ester of hyaluronic acid or on an auto-cross-linked derivative of hyaluronic acid, used singly or in mixtures with one another, characterized by high biocompatibility. The materials are also completely biodegradable and do not need to be removed from the application site, thus avoiding a second surgical operation. When prepared in the form of gels, the cross-linked derivatives present materials with significantly greater viscosity than the unmodified polymer and with variable degradation times.

The term "hyaluronic acid" is used in literature to designate an acidic polysaccharide with various molecular weights constituted by resides of D-glucuronic acid and N-acetyl-D-glucosamine, which naturally occur in cellular surfaces, in the basic extracellular substances of the connective tissues of vertebrates, in the synovial fluid of joints, in the vitreous humor of the eye, in the tissue of the human umbilical cord and in cocks' comb.

Hyaluronic acid plays an important role in the biological organism, firstly as a mechanical support of the cells of many tissues, such as the skin, the tendons, the muscles and cartilage and it is therefore the main component of the extracellular matrix. But hyaluronic acid also performs other functions in the biological processes, such as the hydration of tissues, lubrication, cellular migration, cell function and differentiation. (See for example, A. Balazs et al., Cosmetics & Toiletries, No. 5/84, pages 8–17). Hyaluronic acid may be extracted from the above-mentioned natural tissues, such as cocks' combs, or also from certain bacteria.

Today, hyaluronic acid may also be prepared by microbiological methods. The molecular weight of whole hyaluronic acid obtained by extraction is in the region of 8–13 million Daltons. However, the molecular chain of the polysaccharide can be degraded quite easily under the influence of various physical and chemical factors, such as mechanical influences or under the influence of radiation, hydrolyzing, oxidizing or enzymatic agents. For this reason, often in the ordinary purification procedures of original extracts, degraded fractions with a lower molecular weight are obtained. (See Balazs et al., cited above). Hyaluronic acid, its molecular fractions and the respective salts have been used as medicaments and their use is also proposed in cosmetics (see for example, the above-mentioned article by Balazs et al., and the French Patent No. 2478468).

Although the term "hyaluronic acid" is commonly used in an improper sense, meaning, as can be seen from above, a whole series of polysaccharides with alternations of residues of D-glucuronic acid and N-acetyl-D-glucosamine with varying molecular weights or even degraded fractions of the same, and although the plural form "hyaluronic acids" may seem more appropriate, the discussion herein shall continue to use the singular form to refer to hyaluronic acid in its various forms including its molecular fractions.

The present invention describes injectable compositions containing hyaluronic acid derivatives which work as suitable carriers for biological/pharmacological cells or molecules. Hyaluronic acid derivatives are certainly more suitable than other biomaterials/scaffolds known in the prior art. In comparison with biological-derived system, such as, for instance, cadaveric acellular material, hyaluronic acid has the advantage to be readily available in unlimited supply and not highly immunogenic, such as allogeneic donor tissues. In addition, hyaluronic acid is not at risk for cross-contamination for infective diseases, especially virus derived (HIV, Hepatitis, etc.). In comparison with more purified biological-derived molecules, such as, for instance collagen, proteoglycans and fibrin, or biocompatible synthetic polymers, such as, for instance, PLLA/PGA, PTFE, hyaluronic acid has different favourable characteristics. First of all, hyaluronic acid is a polysaccharide which shows less immunogenic reactions than common proteic- of proteic-based compounds. Secondly, hyaluronic acid is commonly found in all mammals species with no modification of the molecular structure, thus, is very well known and tolerated by the human body. Third, hyaluronic acid has many biological effects, in developing as well as adult humans, which make the molecule to be fundamental in each reparative/regenerative process. Finally, another favourable point is that hyaluronic acid is present in almost all tissues/organs of the human body, being a major component of the extracellular matrix. This fact, along with the simple composition of the polymer, make hyaluronic acid different from many proteic extracellular matrix molecules, such as, for instance collagen, that are, very often, tissue/organ specific. This last point is very important in designing a general and biocompatible delivery vehicle to be used for different compartment of the human body.

2. The Benzyl Ester Derivatives

The first preferred material of the invention is based on the benzyl ester of hyaluronic acid, particularly the 50–75% esters wherein 50% to 75% of the hyaluronic acid carboxyl groups are esterified with a benzyl residue. Those benzyl esters wherein 50–75% of the hyaluronic acid carboxyl groups are esterified with a benzyl group are referred to as "partial esters", because only a portion of the carboxyl groups are esterified and the remaining carboxyl groups are either free or salified with an alkaline or alkaline earth metal, such as sodium, calcium or potassium.

Most preferred for the compositions of the invention are the benzyl esters wherein 50% of the hyaluronic acid carboxy groups are esterified. The benzyl esters of hyaluronic acid according to the invention may be prepared by methods known per se for the esterification of carboxylic acids, for example by treatment of free hyaluronic acid with the alcohol (benzyl alcohol) in the presence of catalyzing substances, such as strong inorganic acids or ionic exchangers of the acid type, or with an etherifying agent capable of introducing the desired alcoholic residue in the presence of inorganic or organic bases.

The benzyl hyaluronic esters may, however, be preferably prepared to advantage according to a particular method described in EP 0 216 453. This method consists of treating a quaternary ammonium salt of hyaluronic acid with an etherifying agent, preferably in an aprotic organic solvent.

For the preparation of the benzyl esters it is possible to use hyaluronic acids of any origin, such as for example, the acids extracted from the above mentioned natural starting materials, for example, from cocks' combs. The preparation of such acids is described in literature; preferably, purified hyaluronic acids are used. According to the invention, especially used are hyaluronic acids comprising molecular fractions of the integral acids obtained directly by extraction of the organic materials with molecular weights varying within a wide range, for example, from about 90%–80% (M=11.7–10.4 million Daltons) to 0.2% (M=30,000 Daltons) of the molecular weight of the integral acid having a molecular weight of 13 million Daltons, preferably between 5% and 0.2%. Such fractions may be obtained with various procedures described in literature, such as by hydrolyzing, oxidizing, enzymatic or physical procedures, such as mechanical or radiational procedures. Primordial extracts are therefore often formed during these same purification procedures (for example, see the article by Balazs et al., quoted above in "Cosmetics & Toiletries"). The separation and purification of the molecular fractions obtained are brought about by known techniques, for example by molecular filtration.

One fraction of purified hyaluronic acid suitable for use according to the invention is for example that known as "non-inflammatory-NIF-NaHA" sodium hyaluronate described by Balazs in the booklet "Healon"—A guide to its use in Ophthalmic Surgery, D. Miller & R. Stegmann, eds. John Wiley & Sons, N.Y., 81983: p 5.

Particularly important as starting materials for the benzyl ester are two purified fractions obtainable from hyaluronic acid, for example the ones extracted from cocks' combs, known as "Hyalastine" and "Hyalectin". The fraction Hyalastine has an average molecular weight of about 50,000 to 100,000 Daltons while the fraction Hyalectin has an average molecular weight of between about 500,000 and 730,000 Daltons. A combined fraction of these two fractions has also been isolated and characterized as having an average molecular weight of about 250,000 to about 350,000 Daltons. This combined fraction may be obtained with a yield of 80% of total hyaluronic acid available in the particular starting material, while the fraction Hyalectin may be obtained with a yield of 30% and the fraction Hyalastine with a yield of 50% of the starting hyaluronic acid. The preparation of these fractions is described in EP 0 138 572.

The following Examples describe the preparation of the benzyl esters of hyaluronic acid.

EXAMPLE 1

Preparation of the 50% Benzyl Ester of Hyaluronic Acid—50% of Esterified Carboxylic Groups—50% of Salified Carboxylic Groups (Na)

12.4 g of hyaluronic acid tetrabutylammonium salt with a molecular weight of 170,000 Daltons corresponding to 20 milliequivalent of a monomeric unit are solubilized in 620 ml of dimethysulfoxide at 25° C., 10 milliequivalent.) of benzyl bromide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30°. 8.6 g of the partial benzyl ester compound in the title are obtained. Quantitative determination of the ester groups is carried out using the method of R. H. Cundiff and P. C. Markunas [Anal. Chem. 33, 1028–1030, (1961)].

EXAMPLE 2

Preparation of the 75% Benzyl Ester of Hyaluronic Acid—75% of Esterified Carboxylic Groups—25% of Salified Carboxylic Groups (Na)

12.4 g of hyaluronic acid tetrabutylammonium salt with a molecular weight of 250,000 Daltons corresponding to 20 milliequivalent of monomeric unit are solubilized in 620 ml of dimethylsufoxide at 25°, 2.5 g (15 milliequivalent) of benzyl bromide are added and the resulting solution is kept for 12 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 9 g of the partial benzyl ester compound in the title are obtained. Quantitative determination of the ester groups is carried out using the method of R. H. Cundiff and P. C. Markunas [Anal. Chem. 33, 1028–1030, (1961)].

EXAMPLE 3

Preparation of the 75% Ester of Hyaluronic Acid— 75% of Esterified Carboxylic Groups—25% of Salified Carboxylic Groups (Na)

12.4 g of hyaluronic acid tetrabutylammonium salt with a molecular weight of 80,000 Daltons corresponding to 20 milliequivalent of a monomeric unit are solubilized in 620 ml of dimethylsufoxide at 25°, 2.5 g (15 milliequivalent) of benzyl bromide are added and the resulting solution is kept for 12 hours at 30°.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30°.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30°. 9 g of the partial benzyl ethyl ester compound in the title are obtained. Quantitative determination of the ester groups is carried out using the method of R. H. Gundiff and P. C. Markunas [Anal. Chem. 33, 1028–1030, (1961)].

3. The Auto (or Internal) Cross-Linked Hyaluronic Acid Derivatives (ACP Derivatives)

The auto cross-linked hyaluronic acid derivatives used in the materials of the present invention are described in EP 0 341 745. These cross-linked derivatives are inter and/or intramolecular esters of hyaluronic acid wherein a part of the carboxy groups are esterified with hydroxyl groups of the same molecule and/or of different molecules of hyaluronic acid, thus forming lactone or intermolecular ester bonds. These "inner" esters, in which there is no intervention by OH groups of other alcohols, can also be defined as "auto-crosslinked hyaluronic acid" (also referred to as "ACP") since the formation of a mono- or polymolecular cross-link is the consequence of the above-mentioned internal esterification. The adjective "cross-linked" refers to the crosswise connections between the carboxyls and hydroxyls of the hyaluronic acid molecules.

The auto-crosslinked products are particularly partial inner esters wherein the percentage of "cross-links" varies preferably between 3 to 15% of the number of carboxy groups in the hyaluronic acid. In the preparation process, the carboxy groups of the hyaluronic acid molecule are activated by the addition of substances capable of inducing such activation. The unstable intermediate products obtained from the activation reaction separate spontaneously, either after the addition of catalysts and/or following a rise in temperature, forming the above mentioned inner ester bonds with hydroxyls of the same or other hyaluronic acid molecule. According to the degree of inner esterification desired, either all or an aliquot part of the carboxy functions are activated (the aliquot part being obtained by using an excess of activating substances or by suitable dosing methods).

The carboxy groups to be converted into inner ester groups can be activated starting from hyaluronic acid containing free carboxy groups, or, preferably, from hyaluronic acid containing salified carboxy groups, for example, metal salts, preferably alkaline or alkaline earth metals, and above all with quaternary ammonium salts, such as those described hereafter. Salts with organic basis such as amines can, however, also be used as starting substances.

Methods for the activation of free or salified carboxy groups are per se known, particularly in the field of peptide synthesis, and those skilled in the art can easily determine which method is the most suitable, especially whether or not to use the starting substances in their free or salified form. Activation methods per se known for peptide synthesis procedures and useful in the preparation procedures of the present invention are described, for example, in Bodanszky, M., In search of new methods in peptide synthesis, Int. J. Peptide Protein Res. 25, 1985, 449–474; and Gross, E. et al, The Peptides, Analysis Synthesis, Biology, Academic Press, Inc., 1979, Vol. 1, Chapter 2. According to such procedures, a carboxyl component is activated, that is, a carboxyl component is converted to a reactive form. Such activation typically involves a reaction between an acid and an activating agent according to the scheme:

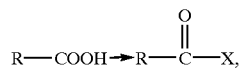

wherein X is an electron withdrawing moiety. Most activated derivatives of carboxylic acids, therefore, are mixed anhydrides, including in the broad sense also acid azides and acid chlorides which can be considered mixed anhydrides of hydrazoic acid and HCl as the activating agents. In addition, activation of a carboxyl component can be accomplished by the formation of intermediate "activated esters". These "activated esters" can be of various types, but particularly useful "activated esters" are those prepared by use of dicyclohexylcarbodiimide, p-nitrophenyl esters, trichlorophenyl esters, pentachlorophenyl esters, and 0-acyl derivatives of hydroxylamines, particularly esters of N-hydroxysuccinimide.

All of these various types of activation procedures are useful in the preparation of the cross-linked hyaluronic acid of the invention, as all of these procedures can be characterized as importantly involving the reaction of a carboxyl group with an activating agent which essentially results in the formation of a substituent group that is easily reactive with a hydroxyl group so as to easily form the inner ester bonding characteristic of the products of the invention, the number of carboxy functions to be converted into inner esters in proportion to the number of activated carboxy functions and this number depends on the quality of the activating agent used.

The preferred procedure for preparation of cross-linked hyaluronic acid is therefore characterized by treating hyaluronic acid, having free or salified carboxy groups, with an agent which activates the carboxy function, possibly in the presence of an auxiliary agent favoring the formation of intermediate activated derivatives and/or a tertiary organic or inorganic base, exposing the mixture to heating or irradiation (particularly with UV light), and if desired, by salifying free carboxy groups or by freeing salified carboxy groups. Of the substances able to activate the carboxy group, the conventional ones described in literature can be used, for example, those usually used in the synthesis of peptides, except however those which would have the effect of altering or destroying the molecular structure of the starting hyaluronic acid, such as those used for the formation of carboxyl halides. Preferred substances which lead to the formation of activated esters are those, such as, carbodiimides, dicyclohexylcarbodiimide, benzylisopropylcarbodiimide, benzyl-ethyl-carbodiimide; ethoxyacetylene; Woodward's reagent (N-ethyl-5-phenylisoxazolium-3-sulfonate) or halogen derivatives from aliphatic, cycloaliphatic or aromatic hydrocarbons, or from heterocyclic compound with halogen made mobile by the presence of one or more activating groups, such as chloroacetonitryl and especially the salts of 2-chloro-N-alkylpyridine, such as chloride of 2-chloro-N-methylpyridine or other alkyl derivatives with inferior alkyl groups, such as those with up to 6 carbon atoms. In the place of chloride derivatives, other halogen derivatives can of course be used, such as bromide derivatives.

This activation reaction can be carried out in organic solvents, especially aprotic solvents such as dialkylsulfoxides, dialkylcarboxylamides, such as in particular lower alkyl dialkylsulfoxides, particularly dimethylsulfoxide, polymethylene sulfoxides, such as tetramethylene sulfoxide, dialkyls or polymethylene sulfones, such as tetramethylene sulfone, sulfolane and lower alkyl dialkyamides of lower aliphatic acids in which the alkyl groups have a maximum of six carbon atoms, such as dimethyl or diethyl formamide or dimethyl or diethyl acetamide. Other solvents may also be used, however, and these need not always be aprotic, such as alcohols, ethers, ketones, esters, such as lower aliphatic dialkyloxyhydrocarbides, such as dimethoxyethane and especially aliphatic or heterocyclic alcohols and ketones with a low boiling point, such as lower N-alkyl-pyrrolidones, such as N-methylpyrrolidone or N-ethyl-pyrrolidone, hexafluorisopropanol and trifluoroethanol. If halogen derivatives are used as carboxyl-activating substances, especially in the form of salts, such as the above-mentioned 2-chloro-N-methylpyridinium chloride, it is better to use a metal salt or a salt of the organic base of the starting polysaccharide, especially one of the quaternary ammonium salts described hereafter, such as tetrabutyl ammonium salt. These salts have the special advantage of being very soluble in the above said organic solvents in which the cross-linking reaction is best effected, thus guaranteeing an excellent yield. It is advisable to add to the mixture a substance capable of subtracting acid, such as organic bases, carbonates, bicarbonates or alkaline or alkaline earth acetates, or organic bases and especially tertiary bases such as pyridine and its homologues, such as collidine, or aliphatic amine bases, such as triethylamine or N-methylpiperazine.

The use of quaternary ammonium salts represents a particularly advantageous procedure. Such ammonium salts are well known and are prepared in the same way as other known salts. They derive from alkyls having preferably between 1 and 6 carbon atoms. It is preferable to use tetrabutyl ammonium salts. One variation in the procedure in which quaternary ammonium salts are used, consists in reacting an alkaline salt, for example, sodium or potassium salt, in the presence of catalyzing quantity of a quaternary ammonium salt, such as tetrabutylammonium iodide.

The substances which catalyze activation of the carboxy groups to be added to the activating agents are reported in literature and these too are preferably bases such as those mentioned previously. Thus, for example, when the carboxy groups are activated with isothiazoline salts it is preferable to add some triethylamine to the reaction mixture.

The reaction of formation of activated intermediates, such as and especially esters, is carried out at the temperature recommended in literature and this temperature can, however, be varied should circumstances require as can be easily determined by one skilled in the art. The formation of inner ester bonds can come about within a fairly wide temperature range, for example between 0° and 150°, preferably room temperature or slightly above, for example between 20° and 75°. Raising the temperature favors the formation of inner ester bonds, as does exposure to radiations of suitable wavelength, such as ultraviolet rays.

The substrate of hyaluronic acid can be of any origin, and can be of the various types discussed above. The preferred hyaluronic acid starting materials are those with an average molecular weight of 150,000 to 730,000 Daltons, especially 150,000 to 450,000 Daltons.

In addition, the amount of internal cross-linking can vary, but preferred materials according to the invention utilize hyaluronic acid cross-linked to a degree of 3 to 15% of the carboxyl groups.

When prepared in the form of gels, the cross-linked dervatives have greater viscosity than the unmodified hyaluronic acid. By controlling the viscosity, both the degradation time and effect on adhesion prevention can be varied. Preferred are those gels having a viscosity of at least 200 $Pa^*sec^{-1}$. More preferred are gels with a viscosity of at least 250 $Pa^*sec^{-1}$ or even 300 $Pa^*sec^{-1}$ and most preferred are those gels having a viscosity of at least 350 $Pa^*sec^{-1}$ or 400 $Pa^*sec^{-1}$.

The following Examples describe the preparation of useful cross-linked hyaluronic acid products for making the materials of the invention.

EXAMPLE 4

Preparation of 3% Cross-Linked Hyaluronic Acid

Product description:

3% of carboxy groups used in internal esterification.

97% of carboxy groups salified with sodium.

6.21 g of hyaluronic acid tetrabutylammonium salt with a molecular weight of 170,000 Daltons corresponding to 10 milliequivalent of a monomeric unit are solubilized in 248 ml of DMSO at 25° C., 0.03 g (0.3 milliequivalent) of triethylamine are added.

A solution of 0.076 g (0.3 milliequivalent) of 2-chloro-1-methyl pyridinium chloride in 60 ml of DMSO is slowly added drop by drop over a time interval of 1 hour and the mixture is kept for 15 hours at 30° C.

A solution formed by 100 ml of water and 2.5 g of sodium chloride is then added and the resulting mixture is then poured slowly into 750 ml of acetone, maintaining continual agitation. A precipitate is formed which is then filtered and washed three times in 100 ml of acetone water 5:1 and three times with 100 ml of acetone and lastly vacuum-dried for 24 hours at 30°.

4 g of the title compound are obtained. Quantitative determination of the ester groups is carried out according to the saponification method described on pp. 169–172 of "Quantitative Organic Analysis Via Functional Groups", 4th Edition, John Wiley and Sons Publication.

EXAMPLE 5

Preparation of 5% Cross-Linked Hyaluronic Acid (ACP 5%)

Product description:

5% of carboxy groups used in internal esterification.

95% of carboxy groups salified with sodium.

6.21 g of hyaluronic acid tetrabutylammonium salt with a molecular weight of 95,000 Daltons corresponding to 10 milliequivalent of a monomeric unit are solubilized in 248 ml of DMSO at 25° C., 0.051 gr (0.5 milliequivalent) of triethylamine are added and the resulting solution is agitated for 30 minutes.

A solution of 0.128 gr (0.5 milliequivalent) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone water 5:1 and three times with 100 ml of acetone and lastly vacuum-dried for 24 hours at 30°.

3.95 grs of the title compound are obtained. Quantitative determination of the ester groups is carried out according to the saponification method described on pp. 169–172 of "Quantitative Organic Analysis Via Functional Groups", 4th Edition, John Wiley and Sons Publication.

EXAMPLE 6

Preparation of 10% Cross-linked Hyaluronic Acid

Product description:

10% of carboxy groups used in internal esterification.

90% of carboxy groups salified with sodium.

6.21 g of hyaluronic acid tetrabutylammonium salt with a molecular weight of 620,000 Daltons corresponding to 10 milliequivalent of a monomeric unit are solubilized in 248 ml of DMSO at 25° C. 0.101 gr (1.0 milliequivalent) of triethylamine is added and the resulting solution is agitated for 30 minutes.

A solution of 0.255 gr (1.0 milliequivalent) of 2-chloro-1-methyl-pyridinium chloride in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed when is then filtered and washed three-times in 100 ml of acetone water 5:1 and three times with 100 ml of acetone and lastly vacuum-dried for 24 hours at 30°.

3.93 grs of the title compound are obtained. Quantitative determine of the ester groups is carried out according to the saponification method described on pp. 169–172 of "Quantitative Organic Analysis Via Functional Groups", 4th Edition, John Wiley and Sons Publication.

EXAMPLE 7

Preparation of 15% Cross-linked Hyaluronic Acid

Product Description:

15% of carboxy groups used in internal esterification.

85% of carboxy groups salified with sodium.

6.21 gr of hyaluronic acid tetrabutylammonium salt with a molecular weight of 170,000 Daltons corresponding to 10 milliequivalent of a monomeric unit are solubilized in 248 ml of DMSO at 25° C, 0.152 gr (1.5 milliequivalent) of triethylamine chloride are added and the resulting solution is agitated for 30 minutes.

A solution of 0.382 g (1.5 milliequivalent) of 2-chloro-1-methyl-pyridinium-chloride in 20 ml of DMSO is slowly added drop by drop over a time interval of 1 hour and the mixture is kept at a temperature of 30° for 45 hours.

A solution made up of 100 ml of water and 2.5 of sodium chloride is added and the resulting mixture is slowly poured into 750 ml of acetone, maintaining continual agitation. A precipitate is formed which is then filtered and washed three times with 100 ml of acetone/$H_2O$ 5:1 and three times with 100 ml of acetone finally vacuum-dried for 24 hours at a temperature of 30°.

3.9 g of the title compound are obtained. Quantitative determination of the total ester groups is carried out according to the saponification method described on pp. 169–172 of "Quantitative Organic Analysis Via Functional Groups", 4th Edition, John Wiley and Sons Publication.

4. The Mammalian Cell and/or Molecular Component

The compositions of the invention are particularly useful in providing an optimal delivery system for the local application of cells and/or biological and/or pharmacological molecules. Many pathologies are due to the significant loss of substance which is barely self-repaired by natural host-driven mechanisms or even not repaired at all. In almost all cases, the repair yields a tissue not equal, in terms of biological, histological and functional characteristics, of the original undamaged tissue. In this regard, Tissue Engineering, that is the combination of cells embedded or layered onto a biocompatible scaffold, offers now the possibility to build in vitro a tissue-like structure which can undergo further maturation/differentiation once grafted into the patient with the potential to completely regenerate the original lost tissue (ref.: Langer and Vacanti, Science, 1993).

In other pathologies, the ability of tissue/organ to function properly or to recover from a specific disease relies on the application of certain biologically active molecules, such as, for instance, growth factors (such as those per se known in the art), or pharmacological substances, such as, for instance, antibiotics which are known in the art. The major difficulty in applying such a drug-based therapy is the correct delivery of said molecules which must reach the specific target and act within a specific window in order to maximize the expected curative effect and, in same cases, decrease the toxic potential toward other tissues/organs.

Yet other pathologies may require a much more complex treatment approach. In particular, specific diseases, such as, for instance, dysmetabolic conditions, need not only a local delivery of curative drug, but also a bio-interactive control in the administration of the substance. One paradigmatic example is constituted by the treatment of insulin-dependent diabetes (type I). The success of any therapeutic protocol is based on the administration of insulin only when haematic glucose levels reach specific values. In this case, only a biological sensible system making insulin may appropriately respond to the body needs. In the particular case, since pancreatic islet cells are actually not easily manipulable with cell culture technology, other cell types, for instance fibroblasts, can be genetically modified in order to express insulin in a regulated fashion. For these specific diseases, the ideal clinical protocol should be constituted by the local delivery of cells, previously committed to produce the specific biological/pharmacological molecule, in a suitable carrier. The cells deliverable by the present invention are mammalian cells, especially those selected from the group consisting of chondrocytes, osteocytes, fibroblasts, keratinocytes, adipocytes, muscle cells, nerve cells, cells from the peripheral nervous system, endothelial cells, hematopoietic cells, glandular cells, cells of the urethra and stem cells, both from adult and embryonic tissue.

For example, the chondrogenic cells may be isolated directly from pre-existing cartilage tissue, for example, hyaline cartilage, elastic cartilage, or fibrocartilage. Specifically, chondrogenic cells may be isolated from articular cartilage (from either weight bearing or non-weight bearing joints), costal cartilage, nasal cartilage, auricular cartilage, tracheal cartilage, epiglottic cartilage, thyroid cartilage, arytenoid cartilage and cricoid cartilage. Methods for isolating chondrogenic cells from such tissues are set forth hereinbelow. Alternatively, chondrogenic cells may be isolated from bone marrow. See for example, U.S. Pat. Nos. 5,197,985 and 4,642,120, and Wakitani et al. (1994) J. Bone Joint Surg. 76:579–591, the disclosures of which are incorporated by reference herein.

Once chondrogenic cells have been isolated from the pre-existing tissue they are proliferated ex vivo in monolayer culture using conventional techniques well known in the art. See for example, Pollack (1975) in "Readings in Mammalian Cell Culture", Cold Spring Harbor Laboratory Press, Cold Spring Harbor, the disclosure of which is incorporated by reference herein. Briefly, the population of chondrogenic cells is expanded by culturing the cells as monolayers and by serially passaging the cells. The chondrogenic cells are passaged after the cells have proliferated to such a density that they contact one another on the surface of the cell culture plate. During the passaging step, the cells are released from the substratum. This is performed routinely by pouring a solution containing a proteolytic enzyme, i.e, trypsin, onto the monolayer. The proteolytic enzyme hydrolyzes proteins which anchor the cells on the substratum. As a result, the cells are released from the surface of the substratum. The resulting cells, now in suspension, are diluted with culture medium and replated into a new tissue culture dish at a cell density such that the cells do not contact one another. The cells subsequently reattach onto the surface of the tissue culture and start to proliferate once again. Alternatively, the cells in suspension may be cryopreserved for subsequent use using techniques well known in the art. See for example, Pollack (supra).

The cells are repeatedly passaged until enough cells have been propagated to prepare a piece of synthetic cartilage of pre-determined size. As a result, a population containing a small number of chondrogenic cells originally isolated from a biopsy sample may be expanded in vitro thereby to generate a large number of chondrogenic cells for subsequent use in the practice of the invention.

In another preferred embodiment, polypeptide growth factors may be added to the chondrogenic cells in the pre-shaped well to enhance or stimulate the production of cartilage specific proteoglycans and/or collagen. Preferred growth factors include, but are not limited to, transforming growth factor-beta (TGF-.beta.), insulin-like growth factor (IGF), platelet derived growth factor (PDGF), epidermal growth factor (EGF), acidic or basic fibroblast growth factor (aFBF or bFBF), hepatocytic growth factor (HGF), keratinocyte growth factor (KGF) the bone morphogenic factors (BMPs) including: BMP-1; BMP-2; BMP-3; BMP4; BMP-5; and BMP-6 and the osteogenic proteins (OPs) including: OP-1; OP-2; and OP-3. In addition, it is contemplated that ascorbate may be added to the chondrogenic cells in the pre-shaped well to enhance or stimulate the production of cartilage specific proteoglycans and collagen. However, these particular compounds are not limiting. Any compound or composition capable of stimulating or inducing the production of cartilage specific proteoglycans and collagen may be useful in the practice of the instant invention.

4.1 Procedures for Isolation of Chondrocytes

Briefly, tissue containing chondrogenic cells is disaggregated to release denuded chondrogenic cells from their extracellular matrix. The denuded cells then are isolated and proliferated as monolayers in an undifferentiated state ex vivo. The passaging procedure may be repeated multiple times (n), for example up to about 7 to 10 passages until enough cells have been propagated to prepare a piece of cartilage of pre-determined size. These steps expand the number of chondrogenic cells in a population that can be used subsequently to form the three-dimensional, multi cell-layered patch of synthetic cartilage.

The proliferated but undifferentiated chondrogenic cells then are seeded into a pre-shaped well having a cell contacting, cell adhesive surface. The cell adhesive surface prevents chondrogenic cells cultured in the well from attaching to the surface of the well. The cells, deprived of anchorage, interact with one another and coalesce within hours to generate a cohesive plug of cells. The chondrogenic cells then begin to differentiate, as characterized by the production and secretion of cartilage-specific markers, i.e., type II collagen and sulfated proteoglycans. Type II collagen is found specifically in cartilage. The chondrogenic cells then are cultured in the well for time sufficient to permit the formation of a three-dimensional, multi cell-layered patch of synthetic cartilage. The resulting synthetic cartilage patch comprises chondrogenic cells dispersed with a new, endogenously produced and secreted extracellular matrix. The extracellular matrix deposited during this procedure is biochemically and morphologically similar to the extracellular matrix found in natural cartilage. Specifically, the synthetic matrix comprises fibers of type II collagen, and sulfated proteoglycans such as chondroitin sulfate and keratan sulfate.

4.2 Isolation of Tissue Containing Chondrogenic Cells

Chondrogenic cells useful in the practice of the instant invention may be sampled from a variety of sources in a mammal that contain such cells, for example, pre-existing cartilage tissue, perichondrial tissue or bone marrow.

Although costal cartilage, nasal cartilage, auricular cartilage, tracheal cartilage, epiglottic cartilage, thyroid cartilage, arytenoid cartilage and cricoid cartilage are useful sources of chondrogenic cells, articular cartilage (from either weight bearing or non-weight bearing joints) is the preferred source. Biopsy samples of articular cartilage may be readily isolated by a surgeon performing arthroscopic or open joint surgery. Procedures for isolating biopsy tissues are well known in the art and so are not described in detailed herein. See for example, "Operative Arthroscopy" (1991) by McGinty et al.; Raven Press, N.Y., the disclosure of which is incorporated by reference herein.

Perichondrial tissue is the membranous tissue that coats the surface of all types of cartilage, except for articular cartilage. Perichondrial tissue provides nutrients to the chondrocytes located in the underlying unvascularized cartilage tissue. Perichondrial tissue sampled from costal (rib) cartilage of patients suffering from osteoporosis provides a source of chondrogenic cells when the normal articular cartilage is diseased or unavailable. Biopsy samples of perichondrial tissue may be isolated from the surface of costal cartilage or alternatively from the surface of auricular cartilage, nasal cartilage and cricoid cartilage using simple surgical procedures well known in the art. See for example: Skoog et al. (1990) Scan. J. Plast. Reconstr. Hand Surg. 24:89–93; Bulstra et al. (1990) J. Orthro. Res. 8:328–335; and Homminga et al. (1990) J. Bone Constr. Surg. 72:1003–1007, the disclosures of which are incorporated by reference herein.

It is contemplated also that chondrogenic cells, specifically mesenchymal cells, useful in the practice of the invention may be isolated from bone marrow. Surgical procedures useful in the isolation of bone marrow are well known in the art and so are not described in detailed herein. See for example, Wakitani et al. (1994) J. Bone Joint Surg. 76: 579–591, the disclosure of which is incorporated by reference herein.

4.3. Preparation of Denuded Chondrogenic Cells

Protocols for preparing denuded chondrogenic cells from cartilage tissue, perichondrial tissue, and bone marrow are set forth below.

A. From Articular Cartilage

Articular cartilage, both loaded (weight bearing) and unloaded (non-weight bearing), may be subjected to enzymatic treatment in order to disaggregate the tissue and release denuded chondrogenic cells from the extracellular matrix. Solutions containing proteolytic enzymes, for example, chondroitinase ABC, hyaluronidase, pronase, collagense, or trypsin may be added to articular cartilage tissue in order to digest the extracellular matrix. See for example, Watt & Dudhia (1988) Differentiation 38:140–147, the disclosure of which is incorporated herein by reference.

In a preferred procedure, articular cartilage is initially cut into pieces of about 1 mm in diameter, or less. This is routinely performed using a sterile scalpel. The minced tissue then is disaggregated enzymatically, for example, by the addition of a solution containing 0.1% collagenase (Boehringer Mannheim GmbH, Germany). Approximately 1 ml of collagenase is added per 0.25 ml equivalents of minced tissue. The sample is then mixed and incubated overnight (up to 16 hours) at 37 degree. C., with agitation. Following the overnight digestion, the residual pieces of tissue are harvested by centrifugation, the supernatant removed, and the remaining cartilage pieces redigested by the addition of a solution containing, for example, 0.25% collagenase and 0.05% trypsin (Sigma Chemical Co., St. Louis). Approximately 1 ml of 0.25% collagenase, 0.05% trypsin is added per 0.25 ml equivalents of residual tissue. The sample then is mixed and incubated for 2–4 hours at 37.degree. C., with agitation. Any remaining tissue is pelleted by centrifugation and the cell suspension harvested. The collagenase, trypsin step is repeated 2–4 times or until the tissue is completely disaggregated.

The enzymatic reaction is terminated by the addition of tissue culture medium supplemented with approximately 10% fetal bovine serum (FBS) (Hyclone, Logan, Utah). A preferred cell culture medium includes, for example, Dulbecco's minimal essential medium (DMEM) (Sigma Chemical Co., St. Louis) supplemented with 10% FBS. An alternative cell culture medium includes a 1:1 (vol/vol) mixture of Medium 199 (Sigma Chemical Co., St. Louis) and Molecular Cell Developmental Biology Medium 202 (MCDB 202) (Sigma Chemical Co., St. Louis), respectively, supplemented with 10% FBS. Alternatively, another cell culture medium useful in the practice of the invention includes a 3:1 (vol/vol) mixture of DMEM and Ham's F-12 (F12) (Sigma Chemical Co., St. Louis), respectively, supplemented with 10% FBS. Fractions containing denuded chondrogenic cells are combined, and the cells inoculated into a cell culture dish at a plating density of about $1 \times 10^2$–$5 \times 10^5$ cells/cm$^2$, preferably about $5 \times 10^2$–$1 \times 10^5$ cells/cm$^2$, and most preferably about $1 \times 10^3$–$1 \times 10^4$ cells/cm$^2$, for cell expansion and testing.

Chondrocytes may be isolated from costal cartilage, nasal cartilage, auricular cartilage, tracheal cartilage, epiglottic cartilage, thyroid cartilage, arytenoid cartilage and cricoid cartilage using the aforementioned procedure.

B. From Perichondrial Tissue

Denuded chondrogenic cells preferably are isolated from perichondrial tissue using the same procedure as described in section II A, hereinabove.

Briefly, the tissue is minced into pieces of about 1 mm in diameter, or less. The minced tissue is repeatedly digested with proteolytic enzymes, for example, trypsin and collagenase. The resulting denuded cells are inoculated into a cell culture dish at a plating density of about $1 \times 10^2$–$5 \times 10^5$ cells/cm$^2$, preferably about $5 \times 10^2$ to $1 \times 10^5$ cells/cm$^2$, and most preferably about $1 \times 10^3$–$1 \times 10^4$ cells/cm$^2$ for cell expansion and testing.

Alternatively, a non-destructive procedure may be used to isolate chondrogenic cells from perichondrial tissue. In this procedure, intact explant tissue is placed in a cell culture dish and incubated in growth medium. The chondrogenic cells located within the tissue migrate out of the tissue and onto the surface of the tissue plate where they begin to proliferate. See for example, Bulstra et al. (1990) J. Orthop. Res. 8:328–335, the disclosure of which is incorporated by reference herein. Briefly, pieces of the minced explant tissue are placed into a tissue culture plate containing tissue culture medium. A preferred cell culture medium comprises DMEM supplemented with 10% FBS. The explant tissues are incubated at 37° C., 5% $CO_2$ for 3–7 days. During this time the chondrogenic cells migrate out of the explant tissue and onto the surface of the tissue culture dish. After reattaching to the surface of the plate, the cells start to proliferate again.

C. From Bone Marrow

Chondrogenic cells, specifically mesenchymal cells, may be isolated from samples of bone marrow. Procedures useful for the isolation of mesenchymal cells from bone marrow are well known in the art, see for example: U.S. Pat. Nos. 5,197,985; 4,642,120; and Wakitani et al. (1994, supra).

For example, in a preferred method, a plug of bone marrow may be removed surgically from the mammal of interest and added to cell culture medium. Preferred complete growth media are disclosed in U.S. Pat. No. 5,197,985. The mixture then is vortexed to break up the plug of tissue. The resulting suspension is centrifuged to separate bone marrow cells from large pieces of particulate matter i.e., bone fragments. The cells then are dissociated to give a single cell suspension by forcing the cells through a syringe fitted with a series of 16, 18, and 20 gauge needles. The cells then are plated out into a tissue culture plate at a cell density of about $1\times10^5$–$1\times10^6$ cells/cm$^2$ for selectively separating and/or isolating bone marrow derived mesenchymal cells from the remaining cells present in the suspension.

III. Expansion of Denuded Chondrogenic Cells In Vitro

Chondrogenic cells isolated from cartilage tissue, perichondrial tissue, or bone marrow using the methods described in section II hereinabove may be placed in monolayer culture for proliferative expansion. The process enables one to amplify the number of isolated chondrogenic cells. In principal, the artisan may produce essentially an unlimited number of chondrogenic cells and therefore essentially an unlimited amount of synthetic cartilage. It is appreciated, however, that during proliferative expansion the chondrogenic cells dedifferentiate and lose their ability to secrete cartilage specific extracellular matrix. A procedure to assay whether the undifferentiated cells still retain their chondrogenic potential is described hereinbelow.

4.4 Cell Proliferation

Protocols for proliferating cells by monolayer culture are well known in the art, see for example, Pollack (supra), and so are not described in detail herein.

Briefly, monolayer cultures are initiated by inoculating primary chondrogenic cells, isolated from either cartilage tissue or perichondrial tissue, into a cell culture dish at a plating density density of about $1\times10^2$–$5\times10^5$ cells/cm$^2$, more preferably about $5\times10^2$–$1\times10^5$ cells/cm$^2$ and most preferably about $1\times10^3$–$1\times10^4$ cells/cm$^2$. Chondrogenic cells that have undergone one or more cycles of passaging are also plated out at the same plating densities. Primary chondrogenic cells isolated from bone marrow are plated out into a tissue culture plate at a cell density of about $1\times10^5$–$1\times10^6$ cells/cm$^2$. Chondrogenic cells from bone marrow that have undergone one or more cycles of passaging are plated out at plating densities of about $1\times10^2$–$5\times10^5$ cells/cm$^2$, more preferably about $5\times10^2$–$1\times10^5$ cells/cm$^2$ and most preferably about $1\times10^3$–$1\times10^4$ cells/cm$^2$. The chondrogenic cells subsequently are cultured at 37° C., 5% $CO_2$ in cell culture medium.

A preferred cell culture medium comprises DMEM supplemented with 10% FBS. Alternatively, a cell culture medium comprising a 1:1 (vol/vol) mixture of Medium 199 and MCDB 202, respectively, supplemented with 10% FBS may be used. Still another cell culture medium useful in the practice of the invention comprises a 3:1 (vol/vol) mixture of DMEM and F12, respectively, supplemented with 10% FBS.

Once the cell cultures become confluent, i.e., the cells grow to such a density on the surface of the plate that they contact one another, the cells are passaged and inoculated into a new plate. This may be accomplished by initially removing the cell culture medium overlaying the cells monolayer by aspiration, and washing the cell monolayer with phosphate buffered saline (PBS). The PBS is removed, by aspiration, and a solution containing a proteolytic enzyme, i.e., 0.1% trypsin, then is poured onto the monolayer. The proteolytic enzyme hydrolyzes proteins that anchor the cells onto the surface of the plate thereby releasing the cells from the surface of the plate. The proteolytic enzyme in the cell suspension then is inactivated by adding FBS to the suspension to give a final concentration of 10% (vol/vol). The density of cells in the suspension then is estimated and the cells re-plated into a new cell culture plate at a density of about $1\times10^2$–5 $10^5$ cells, more preferably about $5\times10^2$–$1\times10^5$ cells, and most preferably about $1\times10^3$–$10^4$ cells per cm$^2$. The passaging procedure may be repeated multiple times, for example up to about 7 to 10 times, until enough cells have been propagated to prepare a piece of cartilage of pre-determined size.

It is appreciated that suspensions of proliferated cells may be cryopreserved indefinitely using techniques well known in the art. See for example, Pollack (supra). Accordingly, populations of chondrogenic cells may be stored for subsequent use whenever a necessity arises.

4.5 Assay To Measure Chondrogenic Potential of Proliferated Cells

Undifferentiated chondrogenic cells, expanded in monolayer culture, may be assayed to determine whether they still retain their chondrogenic potential. This may be performed by culturing the cells in a semi-solid medium in a process called agarose culture. This procedure is described in Benya et al. (1982) Cell 30:215–224, the disclosure of which is incorporated by reference herein.

Briefly, proliferated chondrogenic cells are seeded into a solution of warm 2% low melting temperature agarose (LT agarose) (BioRad, Richmond, Calif.). The use of LT agarose permits cells to be seeded into the agarose without thermal damage to the cells. The agarose is cooled to about 39–41° C. prior to the addition of cells. Approximately $1\times10^3$–$1\times10^6$ cells are seeded into 1 ml of the liquid agarose.

The cells are cultured subsequently at 37° C., 5% $CO_2$ for 3–4 weeks in a cell culture medium preferably containing DMEM supplemented with 10% FBS. During this time, the chondrogenic cells replicate to from colonies which start to secrete an extracellular matrix. The resulting colonies have the appearance of small "nodules" embedded within the agarose. The colonies may be counted and the chondrogenic proportion of cells determined histochemically and immunohistochemically using procedures well known in the art.

4.6 Preparation Of Cell Cultures From Bone Marrow Stroma

Bone marrow stroma can be isolated by aspiration from the iliac crest in sterile conditions and according to standard procedures, by means of a heparin-treated plastic tube connected to a 10-ml syringe containing 1 ml of heparin solution (3,000 units/ml). Besides bone marrow itself, it is possible to use stem cells isolated from bone marrow. In this case the medial proximal surface of the tibia (or any other bone) is exposed under anaesthetic through a small incision. The subcutaneous tissue and the periosteum are incised and folded back to expose the bone surface. The tibia is perforated with a 16- or 18-gauge needle and the bone marrow is aspirated through a heparin-treated plastic tube attached to a syringe containing 1 ml of a heparin solution (3,000 units/ml). The aspirated matter is transferred, under sterile conditions, into a 50-ml plastic tube and centrifuged for 10 minutes at 1,300 rpm. The centrifuged cells are washed three times with warm Hank's basic saline solution (HBSS), centrifuged again and suspended in a complete culture medium containing alpha minimum essential medium (α-MEM) enriched with a 1% antibiotic solution (10,000 units of penicillin, 10 mg/ml of streptomycin), 10% foetal bovine serum (FBS), basic fibroblast growth factor (bFGF) (10 ng/ml) and ±dexamethasone (0.4 μg/ml). The cell suspension is poured into a 35-mm Petri capsule at a density of $3$–$5\times10^6$ nucleate cells per cm$^2$. The mesenchymal stem cells are incubated in a complete culture medium at 37° C. in a humidified atmosphere containing 5% $CO_2$ and 95% air.

After four days of primary culture the undifferentiated cells are removed by washing with a phosphate buffer solution. The culture medium is changed every three days.

When the cells reach confluence after about 2–3 weeks, they are removed from the culture container by enzymatic digestion for 7 minutes at 37° C. with trypsin 0.05%, EDTA 0.02%. The reaction is interrupted by the addition of complete culture medium, the cell suspension is transferred to a 50-ml plastic tube and centrifuged for 10 minutes at 1,400 rpm. The cells are resuspended in a culture medium and counted with a haemocytometer.

In order to induce chondrogenesis in the mesenchymal stem cells and bone marrow cells, the mass culture technique is used (initial cell density >1×10$^6$ cells/cm$^2$).

4.7 Preparation of cell cultures from cartilage tissue

A biopsy of joint cartilage is taken by standard surgical procedures.

The specimen of cartilage is disintegrated by enzymatic digestion using a solution of 0.1% collagenase. Approximately 1 ml of collagenase per 0.25 ml of minced tissue is added. The specimen is mixed and incubated for about 16 hours at 37° C. under agitation. Subsequently the fragments of residue tissue are separated by centrifugation and the supernatant is removed. The fragments of remaining cartilage are exposed to enzymatic digestion again in a solution containing 0.25% collagenase and 0.05% trypsin. The specimen is mixed and incubated for 2–4 hours at 37° C. under agitation. The remaining tissue is separated by centrifugation and the treatment is repeated until digestion is complete.

The enzymatic reaction is interrupted by the addition of a culture medium enriched with 10% foetal bovine serum (FBS) or with Dulbecco's minimal essential culture medium enriched with 10% FBS.

The cell suspension is poured into a 35-mm Petri dish at a density of 3–5×10$^6$ cells per cm$^2$.

5. The Pharmaceutically or Biologically Active Component

Since it has been found that the 50–70% benzyl ester of hyaluronic acid and the 3–15% ACP hyaluronic acid derivatives are excellent carries for a delivery system of injectable administration, the biologically or pharmacologically active component can be of any type desired to be administered to a mammal, such as a human patient. Of particular importance as pharmacologically active substances are antibiotics, anti-inflammatory agents, antiseptics, active hormones, anti-tumoral agents, and anti-viral agents which are per se known to those in the art.

The biologically active substances are preferably those which have an effect on the biological process of the mammal or patient. Of particular importance are substances which favor the adhesion of cells to the biomaterial, such as fibronectin, RGD or integrin sequences, the growth factors such as transforming growth factor β (TGFβ), insulin-like growth factor (IGF), platelet-derived growth factors (PDGF), epidermal growth factors (EGF), acid or basic fibroblast growth factors (aFBF or bFBF), hepatocyte growth factor (HGF), keratinocyte growth factor (KGF), bone morphogenic proteins (BMPS) such as BMP-1, BMP-2, BMP-3, BMP-4, BMP-5 and BMP-6 and osteogenic proteins (OPs) such as OP-1, OP-2 and OP-3, the nucleic acids encoding specific genes or gene sequences or gene transcripts such as DNA and RNA, and differentiation/modulation factors.

6. Additional Components

The compositions of the invention are prepared in the form of a gel containing at least one of the benzyl ester or ACP derivatives and at least one biologically or pharmacologically active component and/or mammalian cell. The gel can also contain one or more derivatives of hyaluronic acid in one or more of various forms such as fibers, granules, microspheres, nanospheres, fragments of sponge. These forms can provide anchorage for the mammalian cells of the composition and are preferably comprised of the total benzyl ester hyaluronic acid derivative (HYAFF-11). The forms can preferably be made by the following procedures.

The microspheres are preferentially prepared by the process described in EP0517565. The nanospheres are preferentially prepared by the process described in WO 96/29998. The sponges are preferentially prepared by the process described in U.S. Pat. No. 4,851,521. The fibres can be prepared according to the procedures described in U.S. Pat. Nos. 5,520,916 and 5,824,335.

EXAMPLE 8

Microspheres

A total benzyl ester hyaluronic acid derivative, where all the carboxy groups of HYAFF-11, as described in U.S. Pat. No. 4,851,521 is dissolved in a an aprotic solvent such as dimethylsulfoxide, at a concentration varying between 5 and 10% weight/volume, generally 7% w/v. Once the polymer has solubilized, the mixture obtained will be referred to hereinafter as the disontinuous phase. At the same time, a mixture is prepared in a suitable reactor of high-viscosity mineral oil containing Arlacel®, a non-ionic surface-active agent, at a concentration of 1% w/v.

This mixture will be referred to hereinafter as the continuous phase.

The continuous phase is kept at 25° C. while being stirred at a fixed speed of 1000 RPM, then the discontinuous phase, prepared as previously described, is added to it. In these conditions, emulsification of the two phases is instantaneous. The ratio between the two phases (discontinuous and continuous) is about 1 to 16.

After 15 minutes of stirring, acetylacetate is added. This solvent mixes perfectly with the two phases of the emulsion but it is a nonsolvent for the polymer and the human insulin polypeptide. It has been proven that the volume of extracting solvent needed to obtain complete extraction is two and a half times the total volume of emulsion. To facilitate extraction the stirring speed is set at 1400–1500 RPM for 10 minutes and then lowered to 500 RPM. The suspension thus obtained continues to be stirred while being pumped with a screw pump through a filter press set at 1 atmosphere. Once this filtration is complete, it is pumped through a filter of normal-hexane, this being a solvent with the double action of "drying" the preparation and solubilizing any residue surfactant which may be present on the surface of the microspheres. The product is then put in suitable containers and stored at 4° C.

In these working conditions the resulting mean particle size is 10 μm.

7. Exemplary Compositions According to the Invention

The following represent examples of the composition according to the invention.

EXAMPLE 9

Composition of Gel of Autocross-Linked Hyaluronic Acid (ACP) Containing Fragments of Autocross-Linked Hyaluronic Acid (ACP) or Total Benzyl Ester (HYAFF-11) Sponge and Cells A sponge of ACP (or HYAFF-11) is brought to a temperature of less than −150° C. in liquid nitrogen, pressed and sieved to obtain a granulometry of less than 100 micron. One hundred mg of granules of ACP is mixed with 0.5 ml of ACP.

Five to ten ml of heparin-treated bone marrow is transferred into a sterile syringe (22 gauge) from 10–20 ml containing ACP granules and gel. The mixture is extruded slowly into a second syringe so as to obtain a homogeneous mixture.

The cells can be injected in vivo into the osteochondral defect immediately afterwards or left to adhere to the microparticles for 3–4 hours at 37° C. before implant.

When the cells are previously expanded in vitro for a certain length of time (2–3 weeks), a known number of cells are suspended in a certain volume before mixing the culture with the gel. The volume of the suspension is calculated so as to avoid excessive dilution of the gel.

An alternative method consists in mixing about 1–2 ml of bone marrow and mesenchymal stem cells with a mixture constituted by 100 mg of fragments of sponge and 35 mg of ACP powder inside a sterile syringe (22 gauge). The mixture is kept at 37° C. for 3–4 hours so as to allow the powder to become hydrated and the cells to adhere to the fragments of sponge.

The following Examples describe the preparation and administration of various combinations of the Hyaluronic Acid component previously described and the mammalian cell and/or molecular component. These examples will be applicable to both soft, such as skin, liver, intestine, and hard, bone and cartilage, tissues.

EXAMPLE 10

Treatment of Chondral and Osteochondral Defects with Chondrogenic Cells Embedded in an Injectable Hyaluronate Acid Derivative-Based Gel The intended composition can be made in the form of an injectable gel containing at least one hyaluronic acid derivative wherein the chondrogenic cells are evenly dispersed. The gel can also contain one or more derivatives of hyaluronic acid in various forms such as fibers, granules, microspheres, nanospheres, fragments of sponge, etc. Firstly, the chondrogenic cells, such as, for instance, adult differentiated chondrocytes or undifferentiated mesenchymal stem cells, are harvested from original tissues, that are, for instance, non-weight-bearing articular cartilage and bone marrow stroma. Cells are isolated and expanded with standard cell culture techniques routinely used by whom skilled in the art. When a suitable cell number, based on the defect size and depth, is achieved, cells are detached from culture bidimensional surfaces and embedded in a gel constituted by ACP or HYAFF partial esterified. The relative cross-linking or esterification rate of the hyaluronic acid-based delivery vehicle may vary according to the desired degradation time to be achieved in the patient. Examples of the preparation of the benzyl esters of hyaluronic acid and autocross-linked hyaluronic acid derivatives have been reported previously. The gel can be manipulated mechanically in such a way that cells result evenly dispersed in the carrier. Then, the combination is injected by the use of a sterile syringe and/or arthroscopic device, routinely used by surgeons skilled in the art, to fill the defect size. Due to the property of hyaluronic acid-carrier, cells stay in the defect and start to make an extracellular matrix that will substitute the carrier in the repair/regeneration period. Moreover, differentiation and/or growth factors may be added to the delivered combination of cells and gel in order to commit undifferentiated chondrogenic cells, for instance when using mesenchymal stem cells, or to stimulate the growth of administered cells and/or host cells.

EXAMPLE 11

Treatment of Chondral and Osteochondral Defects with Chondrogenic Cells Embedded in Injectable Hyaluronic Acid Derivatives Solid/Gel Formulations In order to inject a composition of cells which may have made some extracellular matrix molecules or may have been stabilized on an adhesion surface, the carrier can be a mixture of a solid suspension, micro-particles, embedded in a gel. Micro-particles may act not only as anchorage supports for injected cells, but also as anchorage supports for host-derived cells, for those particles not completely covered by previously seeded chondrogenic cells.

This intended composition can be made in the form of an injectable combination of gel containing at least one hyaluronic acid derivative with a solid suspension containing at least an hyaluronic acid-derived particulate wherein the chondrogenic cells are evenly dispersed. Cells are harvested, isolated and expanded as described in Example 11. Then, cells are mixed in a liquid medium containing at least one hyaluronic acid-derivative in form of fibres, granules, microspheres, nanospheres or sponge fragments made of an ACP or a benzyl ester derivative as described above. Cells are allowed to adhere to the micro-particles in a time comprises from 15 minutes up to 48 hours, or better 30 minutes up to 24 hours or more preferably 1 hour to 3 hours at room temperature, in the operating room or even in a more controlled environment such as a cell culture incubator. Then, cells adhered to the micro-particles are embedded in the gel and, eventually, injected as described above. The combination of hyaluronic acid-derived components is such that a ratio between the micro-particle fraction and the gel fraction can be calculated. The optimal ratio is to be trimmed for the specific clinical application and may vary from 9:1 to 1:9 part of micro-particles over the gel.

EXAMPLE 12

Treatment of Bone Non-Unions with Injectable Combination of an Hyaluronic Acid-Derivative Carrier Embedding a Growth Factor Bone non-unions are commonly complications occurring in orthopedic surgery when treating complex bone defects or dysmetabolism-affected patients. Actual state-of-the-art treatments for bone non-unions rely on drug administration or acellular biomaterial application. A relatively recent approach is to use a specific biological factors in order to stimulate host reparative system to overcome conditions that impede bone callus formation. Such biologically active molecules are, for instance, bone morphogenetic proteins (BMPs). However, since substances have to act locally and no to be dispersed by circulation system (vasculature and/or lymphatic), persons skilled in the art are testing various carriers. hyaluronic acid-derived compounds object of this invention are particularly suitable for this indication because hyaluronic acid is not only osteo-conductive but also osteo-inductive. Thus, while releasing a certain amount of BMP, hyaluronic acid can also potentiate the effect of this biologically active protein and favor bone formation.

The formulation to be used for bone ingrowth is either a gel embedding BMP, for instance BMP 2, or a combination of gel and micro-particles embedding BMP. Gel and micro-particles ratio can be trimmed as described above. This latter combination is intended, but not limited to, to stimulate osteogenesis by direct hyaluronic acid action on bone precursors (osteoinduction), and also stimulate osteoconduction by tissue guidance. In addition, by combining, for instance, BMP 2 and a specific antibiotic, bone growth may be protected from infection, a common complication in bone non-unions.

EXAMPLE 13

Treatment of Cutaneous Malformations by Injecting Different Cells in Hyaluronic Acid-Derivatives Based-Gel and Gel/Solid Combinations Cutaneous malformations have a significant impact on a person's life quality, for instance after mastectomy or extensive burn injury of the face. State-of-the-art treatment protocols rely on the administration of tissue-augmentation degradable substances, for example collagen. However, such temporary device do not eliminate permanently the unaesthetic character and need to be administered constantly. A stable augmentation can be achieved only if extracellular matrix is produced in a correct manner in order to re-establish the original skin contour. Cells injected in a liquid suspension are likely to be dispersed either by vascular or lymphatic system, thus loosing the capacity of synthesizing a permanent organized extracellular matrix. A carrier system, which guarantees a temporary stable anchorage to the surrounding tissue until a permanent adhesion occurs, can be constituted by an hyaluronic acid-derivative based-formulation. In addition, hyaluronic acid may, in part, acts directly in stimulating the wound healing process, as known in the literature.

Thus, extra-cellular matrix-producing cells, such as fibroblasts, can be vehicled by embedding them in a hyaluronic acid-derivative based-gel as described above. Fibroblasts are then injected in subcutaneous space and sticked to the site until the natural process of adhesion to the surrounding tissues takes place. In alternative, a combination of micro-particles, on which first to attach fibroblasts embedded within a gel to deliver evenly dispersed cells, can be used. Ratio and compositions of different formulations are described above. Cells other than fibroblasts may be used to fill a cutaneous depression, such as, for instance, mammary glandular cells or adipocytes (either differentiated or uncommitted).

EXAMPLE 14

Treatment of Auto-Immune Diseases with Genetic Engineered Cells Embedded in Injectable Hyaluronate-Derivatives Solid/Gel Formulations Auto-immune diseases are due to a self-reactive response of the immune-system to specific body's factors, such as insulin in juvenile diabetes or cartilage tissue components in rheumatoid arthritis. Auto-immune diseases are chronic pathologies that affect million of people in the world. Current pharmacological protocols are focused on the symptomatology of the disease by giving generic anti-inflammatory substances delivered either locally or systemically with associated complications.

New generation treatments will involve the use of more powerful and specific compound such as, for example, enzymatic inhibitors or receptor antagonists. However, permanent control of the diseases relies on the continuous administration of these substances with the risk of developing drug-related complications. Another forefront solution is constituted, for instance, by the use of genetically transformed cells ex vivo to produce specific biological or pharmacological substances to counteract the immune reaction. In this particular application, cells are to be injected locally and they must maintain their viability for a long time, possibly for the lifetime of the individual. For this purpose, cells must integrate in the application site, and this can be achieved giving a support in which cells are initially delivered and embedded. hyaluronic acid-derivatives described in previous examples can answer to this need, with the particular properties of being accepted in almost all compartment of the human body. Thus, as described before, chondrogenic cells can be harvested and isolated. Then, cells are transfected to express, in a bio-regulated fashion, anti-rheumatoid agents, such as, for instance, anti-IL-1 or anti-TNF-$\alpha$, with techniques routinely used by persons skilled in the art, and expanded. Eventually, cells are delivered in rheumatoid arthritis patients in the same vehicle used previously. Another application of hyaluronic acid-derivatives based-formulations is constituted by the delivery of genetic material for in vivo gene therapy protocols. Using the combinations of hyaluronic acid described in example 10, DNA or RNA may be directly injected in a suitable carrier to transfect defective lung cells, such as those, for instance, involved in the cystic fibrosis disease.

The invention being thus described, it is clear that these methods can be modified in various ways. Said modifications are not to be considered as divergences from the spirit and purposes of the invention and any modifications that would appear evident to an expert in the field come within the scope of the following claims:

What is claimed is:

1. An injectable bio-compatible composition in the form of a gel comprising at least one hyaluronic acid derivative and at least one biologically or pharmacologically active component and mammalian cell(s), wherein said hyaluronic acid derivative is selected from the group consisting of:
   (a) a benzyl ester of hyaluronic acid wherein 50–75% of the carboxy groups are esterified with a benzyl radical, and
   (b) an auto-cross-linked derivative of hyaluronic acid wherein 3–15% of the carboxyl groups of hyaluronic acid are cross-linked to the hydroxyl group of the same or different hyaluronic acid molecule.

2. The injectable biocompatible composition according to claim 1, wherein said benzyl ester is one wherein 50% of the carboxy groups are esterified with a benzyl radical.

3. The injectable biocompatible composition according to claim 1, wherein said mammalian cell is selected from the group consisting of chrondrocytes, osteocytes, fibroblasts, keratinocytes, adipocytes, muscle cells, nerve cells, endothelial cells, hematopoietic cells, glandular cells, cells of the urethra and stem cells, both from adult and embryo, with the proviso that said mammalian cell is not a human embryonic cell.

4. The injectable biocompatible composition according to claim 1, wherein said cells are chondrocytes.

5. The injectable biocompatible composition according to claim 1, wherein said biologically active component is a pharmacologically active component.

6. The injectable biocompatible composition according to claim 5, wherein said pharmacologically active component is an antibiotic, an anti-inflammatory agent, an antiseptic, an active hormone, an anti-tumor agent or an anti-viral agent.

7. The injectable biocompatible composition according to any one of claims 1–6, wherein said pharmacologically active component is a growth factor, or a differentiation/modulation factor.

8. The injectable biocompatible composition according to claim 7, wherein said growth factor is a member selected from the group consisting of transforming growth factor, insulin-like growth factor, platelet-derived growth factor, epidermal growth factor, acid and basic fibroblast growth factor, hepatocyte growth factor, keratinocyte growth factor, bone morphogenic proteins, and osteogenic proteins.

9. The injectable biocompatible composition according to claim 5, wherein said pharmacologically active component is a nucleic acid such as DNA and RNA.

10. The injectable biocompatible composition according to claim 7, which further comprises fibres, granules, micro spheres, nanospheres or sponge fragments of a derivative of hyaluronic acid.

11. The injectable biocompatible composition according to claim 10, wherein said derivative of hyaluronic acid is the total benzyl ester derivative.

12. The injectable biocompatible composition according to claim 3 wherein the nerve cell is a peripheral nerve cell.

* * * * *

UNITED STATES PATENT AND TRADEMARK OFFICE
CERTIFICATE OF CORRECTION

PATENT NO. : 6,699,471 B2
DATED : March 2, 2004
INVENTOR(S) : Radice, Marco et al.

It is certified that error appears in the above-identified patent and that said Letters Patent is hereby corrected as shown below:

<u>Title page,</u>
Item [30], Foreign Application Priority Data, the following is missing:
(30)          Foreign Application Priority Data
December 21, 1998    (IT)………………………..PD 98A000298

Signed and Sealed this

Seventh Day of September, 2004

JON W. DUDAS
*Director of the United States Patent and Trademark Office*